United States Patent [19] [11] 4,067,824
Teng et al. [45] Jan. 10, 1978

[54] GELLED PERFUME

[75] Inventors: James Teng, St. Louis County; Marcella C. Stubits, St. Louis, both of Mo.; Abraham Minton, Rego Park; James H. Baker, Jackson Heights, both of N.Y.

[73] Assignee: Anheuser-Busch, Incorporated, St. Louis, Mo.

[21] Appl. No.: 726,806

[22] Filed: Sept. 27, 1976

[51] Int. Cl.$^2$ .............................................. C11B 9/00
[52] U.S. Cl. .................................... 252/522; 44/7 B; 424/76; 536/69; 536/108
[58] Field of Search ......................... 252/522; 424/76; 260/226; 44/7

[56] References Cited

U.S. PATENT DOCUMENTS

| | | | |
|---|---|---|---|
| 3,824,085 | 7/1974 | Teng et al. | 44/7 B |
| 3,886,125 | 5/1975 | Chromacek | 424/76 |
| 3,940,384 | 2/1976 | Teng et al. | 260/226 |
| 3,954,963 | 5/1976 | Kuderna | 424/76 |
| 3,997,480 | 12/1976 | Singleton et al. | 252/522 |

Primary Examiner—Veronica O'Keefe
Attorney, Agent, or Firm—Gravely, Lieder & Woodruff

[57] ABSTRACT

A gelled perfume formulation comprising conventional perfume oil or a commercial perfume composition and a polymeric carbohydrate derivative which acts as the gelling agent. The gelled formulation is applied on the skin as a smooth thin film. The composition possesses aesthetically pleasing clarity and enduring fragrance. This perfume can be conveniently transported and easily dispensed.

14 Claims, No Drawings

GELLED PERFUME

BACKGROUND OF THE INVENTION

The main products of the fragrance industry have always been concentrated essences in the form of clear alcoholic liquids, commonly known as perfumes, colognes, and toilet waters. From time to time, however, the industry has introduced emulsified and solid forms of fragrance.

The main problem in formulating emulsified fragrances is that of producing a stable emulsion. This is rendered difficult by the high concentration of perfume oil used. The product must not be greasy upon application to the skin and must not leave an oily residue.

Among the commonly used emulsifying agents are the following:

Carboxy vinyl polymers neutralized with alkalis
Fatty acid soaps
Sulfated alcohols
Oleyl ether phosphates
Polyhdric alcohol esters
Polyethylene oxide ethers
Polyethoxylated sorbitan esters
Sorbitan esters
Liquid solutions of lanolin alcohols
Polyethylene glycol esters
Acetylated polyoxyethylene derivatives of lanolin
Nonylphenoxypoly ethyl alcohols
Polyethylene glycol ethers of lanolin alcohol
Ethylene oxide condensate of a propylene oxidepropylene glycol condensate
Ethoxylated cholesterol Combinations of the carboxy vinyl polymer emulsifying agents (e.g. Carbopol 934,940 and 941) are the most versatile and generally yield satisfactory emulsified fragrances. One problem with carboxy vinyl polymer agents is unwanted microbial growth. The use of antimicrobials is called for to prevent mold growth. Depolymerization by ultraviolet light is also a troublesome problem. The use of ultraviolet light absorbers can minimize this problem.

The high concentration of perfume oil used in emulsified fragrances results in unstable emulsions. The higher the concentration of perfume oil, the more difficult is the stabilization of the emulsion.

Viscosity stabilization is another problem frequently encountered in emulsified fragrances. Some formulations become too viscous to flow through the opening of the bottle; others decrease in viscosity to a watery consistency.

Solid colognes are essentially liquid colognes which have been solidified with a gellant, and are usually composed of the following materials:

| | |
|---|---|
| Perfume | 2 – 5% |
| Ethyl Alcohol | 85 – 90% |
| Solidifying Ingredient | 6 – 5% |
| Polyhydric Alcohol | 0 – 5% |
| Water | 5 – 10% |

Hard soaps are used as the solidifying agent. One soap generally used is sodium stearate. The presence of unsaponifiable matter and oleates tends to interfere with gelation. Other solidifying ingredients include rosin soaps, candelilla wax, beeswax, carnauba wax, potassium diacetone fructose sulfate, acetanilide, calcium acetate, and ethyl cellulose.

The inclusion of potassium chloride, castor oil, or castor oil fatty acids is desired for the preparation of clear, transparent gels, but castor oil and its fatty acids tend to reduce the gel strength.

It is an object of this invention to produce a gelled perfume with pleasing clarity and enduring fragrance. It is a further object to produce a gelled perfume that avoids unwanted microbial growth. It is still a further object to produce a gelled perfume that is highly stable and that also has a stable viscosity.

SUMMARY OF THE INVENTION

This invention involves a gelled perfume comprising a conventional perfume base and a polymeric carbohydrate gelling agent. This perfume possesses aesthetically pleasing clarity and enduring fragrance. The perfume can be conveniently carried and easily dispensed.

DETAILED DESCRIPTION

About 0.5 to about 3.5% by weight gelling agent is used in the composition. The gelling agent is prepared by dissolving same in denatured ethyl alcohol (SD-40). Other solvents can be used in place of ethyl alcohol. The alcohol makes up about 45 to about 70% by weight of the final composition.

About 0.1 to about 0.3% by weight of a preservative agent is used in the composition.

About 15 to about 35% by weight of an emollient is also used in the composition.

About 10 to about 18% by weight perfume oil is used in the composition. Conventional perfumes may also be used to provide the perfume oil.

The purpose of the preservative is to prevent mildew. Suitable preservatives are methyl p-hydroxybenzoate, potassium sorbate, and alkyl dimethyl benzyl ammonium chloride.

The purpose of the emollient is to impart a luxurious feel to the gelled perfume application. Suitable agents are isopropyl isostearate, isopropyl myristate, and isopropyl palmitate.

The gelling agent that is employed in this invention can be used with both alcoholic base fragrances and oil base fragrances. The perfumes in the alcoholic base category should contain at least 12 oz. of perfume oil per gallon of alcohol, and the alcohol shall contain no more than 15% water (by volume). A preferred perfume contains 20 oz. of perfume oil per gallon of alcohol, and the alcohol contains 5% (by volume) of water. There are no such limitations for perfumes in the oil base category.

The gelling agent is not suitable for use in lower quality fragrances, e.g., toilet water, cologne, that contain more than 15% water and less than 12 oz. of perfume oil per gallon of alcohol.

Teng et al, U.S. Pat. No. 3,824,085 discloses the gelling agents to be used in this invention. Basically, these gelling agents are polymeric carbohydrate derivatives selected from the group consisting of hydroxypropyl cellulose esters and hydroxypropyl starch esters and mixtures of these esters. These esters can have a degree of substitution (D.S.) of acetyl groups of about 1.2 to about 3 and a degree of molar substitution (M.S.) of hydroxypropyl groups of about 2 to about 8. Suitable esters are hydroxypropyl cellulose acetate
hydroxypropyl starch acetate
hydroxypropyl cellulose laurate
hydroxypropyl starch laurate Teng et al, U.S. Pat. No. 3,940,384 discloses another gelling agent which can be used in this invention. This gelling agent is methyl hydroxypropyl cellulose acetate. This ester has a D.S. of acetyl groups of about 0.8 to about 2.5 and a M.S. of hydroxyl groups of about 2 to about 8. The D.S. of methyl groups is about 0.1 to about 1.0.

The important physical properties of the gelling agent are summarized in Table I. The usual form is that of a white powder of 20–40 mesh. Depending upon the equipment, the particle size can be varied. The material is basically not hygroscopic and therefore has low moisture content.

The gelling agents are highly substituted derivatives and are generally inert to enzymatic activity.

TABLE I

PHYSICAL PROPERTIES OF GELLING AGENT

| | |
|---|---|
| Color | White |
| Physical Form | Soft powder, 20–40 mesh |
| Moisture | 0.5% |
| Ash | 1.0% |
| Specific Gravity | 1.017 |
| Glass Transition Temperature | 85° C |
| Melting Range | 190–210° C |
| Char Point | 240° C |
| Biological Activity | Does not support microbial growth. Inert to proteolytic amylolytic degradation. |

EXAMPLE I 0.025 gm of hydroxypropyl cellulose acetate was dispersed in 2.5 ml of Chantilly perfume (Houbigant), and the dispersion was agitated for approximately 3 minutes on a Vortex Mixer. The resulting clear gel was smooth and highly viscous.

EXAMPLE II 0.04 gm hydroxypropyl starch acetate was dispersed in 4.0 of Wild Musk perfume (Max Factor), and the dispersion was agitated for approximately 5 minutes on a Vortex Mixer. The resulting clear gel had a Brookfield viscosity of approximately 4000 cps.

EXAMPLE III 6 ml of perfume oil, Perry F-73-295, were blended in denatured alcohol (100 ml), SDA 40. To the blend were added 1.8 gm of methyl hydroxypropyl cellulose acetate. The resulting solution was mixed until the gel was formed.

What is claimed is:

1. A perfume formulation consisting essentially of perfume oil dispersed in a base selected from alcohol containing no more than about 15% water and no less than about 12 ounces of perfume oil per gallon of alcohol, oil, or mixtures thereof, and a gelling agent selected from the group consisting of hydroxypropyl cellulose esters, hydroxypropyl starch esters, and mixtures thereof, said esters having a degree of substitution of about 1.2 to about 3 and a degree of molar substitution of hydroxypropyl groups of about 2 to about 8.

2. The product of claim 1 wherein the gelling agent is hydroxypropyl cellulose acetate.

3. The product of claim 1 wherein the gelling agent is hydroxypropyl starch acetate.

4. The product of claim 1 wherein the gelling agent is hydroxypropyl cellulose laurate.

5. The product of claim 1 wherein the gelling agent is hydroxypropyl starch laurate.

6. The product of claim 1 wherein the gelling agent is methyl hydroxypropyl cellulose acetate having a degree of molar substitution of hydroxypropyl groups of about 2 to about 8, a degree of substitution of methyl groups of about 0.1 to about 1, and a degree of substitution of acetyl groups of about 0.8 to about 2.5.

7. The product of claim 1 wherein the gelling agent makes up about 0.5 to about 3.5% by weight of the formulation.

8. The product of claim 1 wherein the perfume oil is dispersed in alcohol at a concentration of at least 12 oz. per gallon, said alcohol having a maximum water content of 15 vol. percent.

9. The product of claim 1 containing about 9 to about 15% by weight perfume oil, about 0.5 to about 3.5% by weight gelling agent, and about 45 to about 70% by weight alcohol.

10. The product of claim 9 including about 0.1 to about 0.3% by weight methyl p-hydroxybenzoate as a preservative and about 15 to about 35% by weight isopropyl isostearate as an emollient.

11. The product of claim 9 wherein the gelling agent is selected from the group consisting of hydroxypropyl cellulose acetate, hydroxypropyl cellulose laurate, hydroxypropyl starch acetate, hydroxypropyl starch laurate, and methyl hydroxypropyl cellulose acetate.

12. The product of claim 1 including a preservative and an emollient.

13. The product of claim 12 wherein the preservative is methyl p-hydroxybenzoate.

14. The product of claim 12 wherein the emollient is isopropyl isostearate.

* * * * *